(12) United States Patent  (10) Patent No.: US 8,107,812 B2
Zhang  (45) Date of Patent: Jan. 31, 2012

(54) DYNAMIC RANGE MEASUREMENT AND CALCULATION OF OPTICAL KEYLESS ENTRY SENSOR

(75) Inventor: Wenwei Zhang, Bellshill (GB)

(73) Assignee: Honeywell International Inc., Morristown, NJ (US)

( * ) Notice: Subject to any disclaimer, the term of this patent is extended or adjusted under 35 U.S.C. 154(b) by 1533 days.

(21) Appl. No.: 11/234,466

(22) Filed: Sep. 23, 2005

(65) Prior Publication Data

US 2007/0071448 A1    Mar. 29, 2007

(51) Int. Cl.
B60R 25/10 (2006.01)
G06M 7/00 (2006.01)
H01L 31/00 (2006.01)

(52) U.S. Cl. ............... 398/17; 398/16; 398/22; 398/25; 359/308; 356/239.2; 356/6; 356/4.02; 356/10; 356/239.8; 356/237.3

(58) Field of Classification Search .............. 359/308; 356/239.2, 4.02, 6, 10, 239.8, 237.3; 398/128–131, 398/16, 22, 25
See application file for complete search history.

(56) References Cited

U.S. PATENT DOCUMENTS

| | | | | |
|---|---|---|---|---|
| 2,004 A * | 3/1841 | Harris et al. | 440/90 |
| 3,045,123 A * | 7/1962 | Frommer | 250/565 |
| 3,761,179 A * | 9/1973 | Plummer et al. | 356/601 |
| 3,816,647 A * | 6/1974 | Chang et al. | 348/161 |
| 3,900,261 A * | 8/1975 | Wingate | 356/5.03 |
| 3,979,589 A * | 9/1976 | Sternberg et al. | 250/252.1 |
| 4,006,358 A * | 2/1977 | Howarth | 250/339.1 |
| 4,176,916 A * | 12/1979 | Carpenter | 359/589 |
| 4,189,233 A * | 2/1980 | Hurt et al. | 356/4.02 |
| 4,197,013 A * | 4/1980 | Van Ackeren et al. | 356/438 |
| 4,262,362 A * | 4/1981 | Kiernan et al. | 398/139 |
| 4,300,811 A * | 11/1981 | Ettenberg et al. | 359/359 |
| 4,342,514 A * | 8/1982 | Mathews | 356/4.02 |
| 4,381,151 A * | 4/1983 | Smith | 356/369 |
| 4,460,259 A * | 7/1984 | Greivenkamp et al. | 396/75 |
| 4,464,115 A * | 8/1984 | Simpson et al. | 434/27 |
| 4,465,929 A * | 8/1984 | Edgar | 250/252.1 |
| 4,627,723 A * | 12/1986 | French et al. | 356/4.02 |
| 4,799,799 A * | 1/1989 | Sapko et al. | 356/446 |
| 4,868,915 A * | 9/1989 | Anderson et al. | 340/5.61 |
| 4,968,137 A * | 11/1990 | Yount | 356/41 |
| 5,025,145 A * | 6/1991 | Lagowski | 250/214 R |
| 5,068,528 A * | 11/1991 | Miller et al. | 250/231.13 |
| 5,083,154 A * | 1/1992 | Terashita et al. | 355/68 |
| 5,282,014 A * | 1/1994 | Ruhl et al. | 356/4.02 |

(Continued)

FOREIGN PATENT DOCUMENTS

DE    4212291    10/1993

(Continued)

Primary Examiner — Danny Leung
(74) Attorney, Agent, or Firm — Seager, Tufte & Wickhem, LLC (57) ABSTRACT

An optical keyless entry sensor system and method includes an optical sensor in association with a mirror that reflects light transmitted from the optical sensor, wherein reflected light is detectable by the optical sensor. An attenuation filter can be located between the mirror and the optical sensor, wherein the attenuation filter is configured to simulate a contamination of the optical sensor in order to determine an exact level of attenuation representative of contamination that causes a performance failure of the optical sensor, thereby providing data which is indicative of a dynamic range of the optical sensor, such that the dynamic range is utilized to enhance the performance of the optical keyless entry sensor system.

19 Claims, 4 Drawing Sheets

U.S. PATENT DOCUMENTS

| | | | | |
|---|---|---|---|---|
| 5,369,495 | A * | 11/1994 | Lagowski | 356/418 |
| 5,371,543 | A * | 12/1994 | Anderson | 348/270 |
| 5,437,030 | A * | 7/1995 | Reitman et al. | 717/164 |
| 5,557,395 | A * | 9/1996 | Uno et al. | 356/28 |
| 5,568,267 | A * | 10/1996 | Sunamori et al. | 356/416 |
| 5,682,135 | A | 10/1997 | Labonde | |
| 5,686,722 | A * | 11/1997 | Dubois et al. | 250/226 |
| 5,745,236 | A * | 4/1998 | Haga | 356/600 |
| 5,747,813 | A * | 5/1998 | Norton et al. | 250/372 |
| 5,773,820 | A * | 6/1998 | Osajda et al. | 250/231.14 |
| 5,966,229 | A * | 10/1999 | Dodley et al. | 398/120 |
| 6,075,294 | A | 6/2000 | Van den Boom et al. | |
| 6,078,042 | A * | 6/2000 | Fellows | 250/252.1 |
| 6,122,084 | A * | 9/2000 | Britz et al. | 398/131 |
| 6,211,947 | B1 * | 4/2001 | Tsuji | 355/67 |
| 6,239,693 | B1 * | 5/2001 | Benard et al. | 340/426.26 |
| 6,303,929 | B1 * | 10/2001 | Oshima et al. | 250/271 |
| 6,345,909 | B1 * | 2/2002 | Yam | 374/2 |
| 6,384,904 | B1 * | 5/2002 | Ohishi et al. | 356/5.13 |
| 6,423,964 | B2 * | 7/2002 | Nakaya et al. | 250/234 |
| 6,553,175 | B2 * | 4/2003 | Jaspan | 385/140 |
| 6,559,999 | B2 * | 5/2003 | Lindner et al. | 359/233 |
| 6,577,226 | B1 | 6/2003 | Steiner | |
| 6,625,558 | B1 * | 9/2003 | Van Ausdall et al. | 702/117 |
| 6,684,012 | B2 * | 1/2004 | Kimura | 385/49 |
| 6,700,690 | B1 * | 3/2004 | Buchsbaum et al. | 359/230 |
| 6,803,593 | B2 * | 10/2004 | Ohishi et al. | 250/559.29 |
| 6,891,651 | B2 * | 5/2005 | Kim et al. | 359/240 |
| 6,906,613 | B1 * | 6/2005 | Tamura | 340/5.64 |
| 6,915,122 | B2 * | 7/2005 | Meradi | 455/297 |
| 7,050,122 | B2 * | 5/2006 | Gibbon et al. | 348/771 |
| 7,103,208 | B2 * | 9/2006 | Wengender et al. | 382/141 |
| 7,106,172 | B2 * | 9/2006 | Neveux et al. | 340/5.72 |
| 7,248,344 | B2 * | 7/2007 | Morcom | 356/10 |
| 7,286,220 | B2 * | 10/2007 | Koeberle et al. | 356/243.6 |
| 7,477,371 | B2 * | 1/2009 | Marxer et al. | 356/237.2 |
| 7,477,373 | B2 * | 1/2009 | Miyakawa et al. | 356/237.3 |
| 7,622,728 | B2 * | 11/2009 | Wuestefeld | 250/559.4 |
| 2002/0093727 | A1 * | 7/2002 | Krummrich | 359/337.1 |
| 2002/0185618 | A1 * | 12/2002 | Ohishi et al. | 250/559.38 |
| 2002/0198673 | A1 * | 12/2002 | Koeberle et al. | 702/108 |
| 2003/0011763 | A1 * | 1/2003 | Taniguchi et al. | 356/239.2 |
| 2003/0189163 | A1 * | 10/2003 | Ueyama et al. | 250/214.1 |
| 2004/0031908 | A1 * | 2/2004 | Neveux et al. | 250/221 |
| 2004/0119981 | A1 | 6/2004 | May | |
| 2005/0017840 | A1 * | 1/2005 | Masudaya | 340/5.64 |
| 2005/0046546 | A1 * | 3/2005 | Masudaya | 340/5.61 |
| 2005/0083175 | A1 * | 4/2005 | Yanagimoto | 340/5.72 |
| 2005/0099263 | A1 * | 5/2005 | Ikeda | 340/5.62 |
| 2005/0140496 | A1 * | 6/2005 | Magner et al. | 340/5.54 |
| 2005/0162254 | A1 * | 7/2005 | Michishige et al. | 340/5.61 |
| 2005/0170332 | A1 * | 8/2005 | Shimamoto | 435/4 |
| 2005/0238279 | A1 * | 10/2005 | Fukuyama et al. | 385/14 |
| 2005/0275844 | A1 * | 12/2005 | Kaltenbacher et al. | 356/418 |
| 2006/0232379 | A1 * | 10/2006 | Shelley et al. | 340/5.62 |
| 2007/0047880 | A1 * | 3/2007 | Okada | 385/92 |
| 2007/0071448 | A1 * | 3/2007 | Zhang | 398/159 |
| 2007/0139657 | A1 * | 6/2007 | Ishimaru et al. | 356/511 |
| 2007/0139769 | A1 * | 6/2007 | DeCusatis et al. | 359/478 |
| 2007/0201324 | A1 * | 8/2007 | Hirono | 369/44.24 |
| 2008/0107420 | A1 * | 5/2008 | Nakaso et al. | 398/130 |
| 2008/0297932 | A1 * | 12/2008 | Uchiyama et al. | 359/888 |

FOREIGN PATENT DOCUMENTS

| | | |
|---|---|---|
| DE | 19843594 | 4/2000 |
| DE | 10330525 A1 | 6/2005 |
| GB | 2336625 | 10/1999 |
| JP | 2001 063190 A | 3/2001 |
| WO | WO 02/02893 A1 | 1/2002 |
| WO | WO 02/002893 A1 | 10/2002 |

* cited by examiner

DYNAMIC RANGE MEASUREMENT AND CALCULATION OF OPTICAL KEYLESS ENTRY SENSOR

TECHNICAL FIELD

Embodiments are generally related to keyless access sensor systems. Embodiments are additionally related to optical keyless entry sensors and systems. Embodiments are also related to methods and systems for measuring the dynamic range of optical keyless entry sensors.

BACKGROUND OF THE INVENTION

It is important, for many reasons, to control access to premises, vehicles and personal property so that only authorized users are allowed access. Typically, this is accomplished using keys that fit into a lock, thereby allowing a user of the key to open the lock and gain entry. One problem with the existing key and lock arrangements is that loss or damage to the key can render access impossible. In addition, if the key lock itself is blocked or damaged, this can also prevent access. One other problem is that the use of a key requires a specific action such as unlocking a latch with the key from the authorized person before an action of opening the door. This specific action is very often not easy to accomplish, and is also time-consuming and not particularly ergonomic in nature.

A number of techniques have been proposed in an attempt to overcome these disadvantages. With security devices for automobiles, for example, it is well known that a keyless component can be used, such that the actuation of a button on the keyless component generates an infrared (IR) or radio frequency (RF) signal that is detected by a sensor in the vehicle, which unlocks the doors. A key is still required by the user in order to operate the ignition system. The keyless component also contains a lock button that generates a similar IR or RF signal to lock the vehicle. Such vehicle keyless access systems have been known for a number of years. Such systems operate on the basis that when the IR or RF "open" signal is generated by the keyless component, the signal is used to actuate a mechanism that unlocks the car door so that when the user pulls on the handle, the door is already unlocked. Similar arrangements may be utilized for building entry systems.

One problem with this arrangement is that the user still has to initiate a specific action such as, in the case of a fob, taking the fob in his hand and pressing on the fob button, or in the case of a magnetic card or the like, inserting the card in a slot or to present it in front of a card reader/detector or the like, in order to unlock the door and have access to the vehicle, these specific actions being time-consuming and not ergonomic.

One other problem with this arrangement is that if the user decides not to enter the vehicle but forgets to actuate the "lock" signal, the car and/or building remains open and is thus vulnerable. In addition, with existing keyless locking systems, particularly for vehicles, a conventional locking mechanism is used which is susceptible to interference by thieves to gain access to the car. For buildings, conventional locks are actuated in the same way and are susceptible to the same procedures by intruders to gain access to the premises.

A passive entry sensor system for use in a keyless access system used in automotive applications transmits a beam of light from a sensor that is bracket-mounted and spaced behind the door skin. The beam of light strikes a lens protector mounted on the door skin, where the beam is deflected towards a mirror mounted on the door handle. On striking the mirror, the beam is reflected back to the lens protector where it is deflected into the sensor and detected. Alternatively, the bracket-mounted sensor can be configured to provide a beam from one end of the handle to the other by optically coupling the bracket-mounted sensor to the handle using light guides.

Optical keyless entry sensors have been utilized in a number of keyless entry sensor applications, particularly in the context of automobiles. One of the advantages of such a sensor is that the sensors can perform properly, even if the optical components of the sensor are seriously contaminated. This feature of an optical keyless entry sensor is referred to as the "dynamic range" value of the sensor. As such optical keyless entry sensors continue to develop, it is important to reduce the cost associated with the manufacturing of such sensors, while also improving performance. One manner for accomplishing both of these goals is to test and thereby enhance the dynamic range value. To date, few methodologies and systems have been designed and implemented, which adequately result in testing the dynamic range value of an optical keyless entry sensor. It is believed that the methodology and systems disclosed herein address this continuing and important need.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the present invention to provide for an improved optical keyless entry method and system.

It another aspect of the present invention to provide for a method and system for testing and measuring the dynamic range value of an optical keyless entry sensor.

The aforementioned aspects and other objectives and advantages can now be achieved as described herein. An optical keyless entry sensor system and method are disclosed. In general, an optical sensor can be provided in association with a mirror that reflects light transmitted from the optical sensor, wherein reflected light is detectable by the optical sensor. An attenuation filter can be located between the mirror and the optical sensor, wherein the attenuation filter is configured to simulate a contamination of the optical sensor in order to determine an exact level of attenuation representative of contamination that causes a performance failure of the optical sensor, thereby providing data which is indicative of a dynamic range of the optical sensor, such that the dynamic range is utilized to enhance the performance of the optical keyless entry sensor system.

The attenuation filter is generally provided as a continuous attenuation neutral density filter. The optical sensor generally includes an optical transmitter and an optical receiver. A plurality of lenses can also be provided, which collimate light transmitted from the optical transmitted and reflected to the optical receiver from the mirror. The optical transmitter can be provided as an infrared light emitting diode, and the optical receiver can be implemented as a photodiode.

The attenuation filter is rotated until sensor optical sensor does not function properly, such that a measurement of a specific rotation angle of the attenuation filter, which is strictly proportional to an attenuation value of the optical sensor, represents the dynamic range of the sensor. The attenuation filter is also located as close as possible to the optical receiver to overcome the cross-talk associated with the optical transmitter and the optical receiver. Additionally, the attenuation filter comprises a side associated with the optical receiver, wherein the side of the attenuation filter is configured to overcome the cross-talk associated with the optical transmitter and the optical receiver.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

DETAILED DESCRIPTION

The particular values and configurations discussed in these non-limiting examples can be varied and are cited merely to illustrate at least one embodiment and are not intended to limit the scope thereof.

Figure 1:
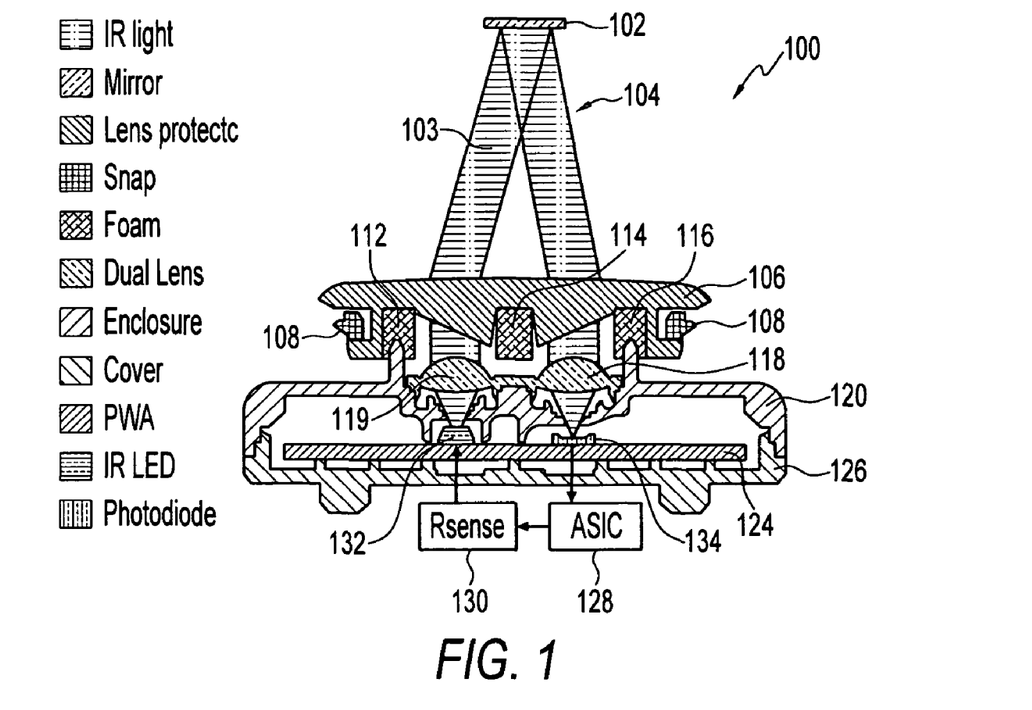
FIG. 1 illustrates a cross-sectional view of an optical keyless entry sensor system, which can be adapted for use in accordance with a preferred embodiment.

FIG. 1 illustrates a cross-sectional view of an optical keyless entry sensor system 100, which can be adapted for use in accordance with a preferred embodiment. In general, the optical keyless entry sensor system 100 includes a mirror 102 located opposite a lens protection component 106. A snap component 108 is positioned adjacent the lens protection component 106 and generally surrounds a plurality of foam pieces 112, 114, and 116. A set of dual lenses 118, 119 is generally located proximate to the lens protection component 106. A PWA component 124 is connected to an IR LED 132 and a photodiode 134. The PWA component 124, the IR LED 132 and the photodiode 124 are generally surrounded and maintained by an enclosure 120.

An Application Specific Integrated Circuit (ASIC) 128 can be utilized, which receives data transmitted from the photodiode 134. The ASIC 128 then transmits this data to a sensing circuit 130, which in turn can transmit information directly to the IR LED 132. Note that the IR LED 132 generally transmits infrared light 103, which is reflected from mirror 102 as reflected light 104, which is detectable by the photodiode 134. The ASIC 128 can be implemented as a circuit designed for a specific application, as opposed to a general purpose circuit, such as a microprocessor. Using ASICs as components in electronic devices can improve performance, reduce power consumption, increase safety and reduce costs.

FIG. 1 thus illustrates the cross section of optical keyless entry sensor 100. IR light 103 from the IR LED 132 is generally collimated by the collimated lens 119 (i.e., here it is one of dual lenses 119, 118). The light 103 then hits the mirror 102 after being bent by the lens protector or lens protection component 106. The reflected light 104 from the mirror 102 goes through the lens protector 106 and one of the dual lenses (i.e., lens 118), and then hits the photodiode 134. Note that in the configuration depicted in FIG. 1, the mirror 102 can be mounted on a handle of an automobile.

In practice, the mirror 102 and the lens protector 106 of the sensor 100 and the optical path between the mirror 102 and the lens protector 106 are exposed to the environment. Contamination on such components may result in a reduction of the dynamic range value of the sensor. In order to overcome these disadvantages, a measurement technique for detecting the dynamic range value of the sensor system 100 can be implemented as follows. First, a quantitative optical attenuator (not shown in FIG. 1) can be placed between the mirror 102 and the lens protector 106, which is simulated as quantitative contamination. Second, it must be determined what exact level contamination (attenuation) could cause performance failure of the sensor 100. Third, the optical attenuation range that permits the sensor 100 to function correctly can represent the dynamic range value of the sensor 100. This means that the sensor 100 can still perform properly if the components of the sensor 100 are contaminated within the measured dynamic range.

Figure 2:
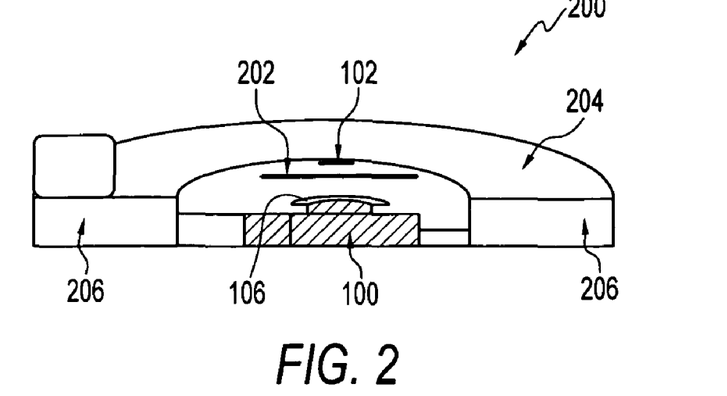
FIG. 2 illustrates a dynamic range measurement system, which can be implemented in accordance with a preferred embodiment.

FIG. 2 illustrates a dynamic range measurement system 200, which can be implemented in accordance with a preferred embodiment. Note that in FIGS. 1-2 identical or similar parts or elements are generally indicated by identical reference numerals. System 200 thus incorporates the use of sensor 100, which was discussed above with respect to FIG. 1. The configuration depicted in FIG. 1 can adapted for use with the system 200 illustrated in FIG. 2. System 200 includes a handle 204, which may be, for example, an automobile door handle. Mirror 102 from the sensor system 100 of FIG. 1 can be incorporated into system 200 and is disposed opposite the lens protector 106.

An attenuation disc 202 is located between the mirror 102 and the lens protector 106. The sensor 100 incorporates the use of lens protector 106 in the same configuration as depicted in FIG. 1. The mirror 102 can be mounted or connected directly to the handle 204, which in turn can be connected to a fixture 206. Note that fixture 206 may form part of, for example, an automobile door handle fixture, depending upon design considerations. System 200 thus presents the basic measurement principles of the dynamic range of a keyless optical sensor (e.g., keyless entry optical sensor systems 100, 300, 400 500 described herein), which can be configured in association with a continuous attenuation neutral density filter or disc 202 that is located between the sensor 100 and the reflection mirror 102.

The disc or filter 202 can be simulated as quantitative contamination of the parts of the sensor 100 in order to work out what exact level contamination (attenuation) could cause performance failure of the sensor. Continuous rotation of the attenuation filter 202 may cause continuous attenuation of lights when the lights pass through the filter 202 and then hits on the mirror 102. The specific rotation angle of the attenuation filter, 202 which is strictly proportional to the attenuation of optical power of the sensor 100, is relevant to the dynamic range value of the sensor 100.

A continuous attenuation neutral density filter may be utilized, which functions as a reflective continuous attenuation neutral density filter rather than absorptive continuous attenuation neutral density filter. This reflective continuous attenuation neutral density filter attenuates the transmission lights by reflecting away the certain amount of the lights. Due to its reflective attenuation property, however, this reflective continuous attenuation neutral density filter could result in a strong reflection effect and may cause significant measurement errors of the dynamic range if it is utilized inappropriately. In order to obtain the accurate measurement value of the dynamic range value of the sensor 100, any sort of reflective lights from the reflective continuous attenuation neutral density filter should not go into the photodiode 134.

Figure 3:
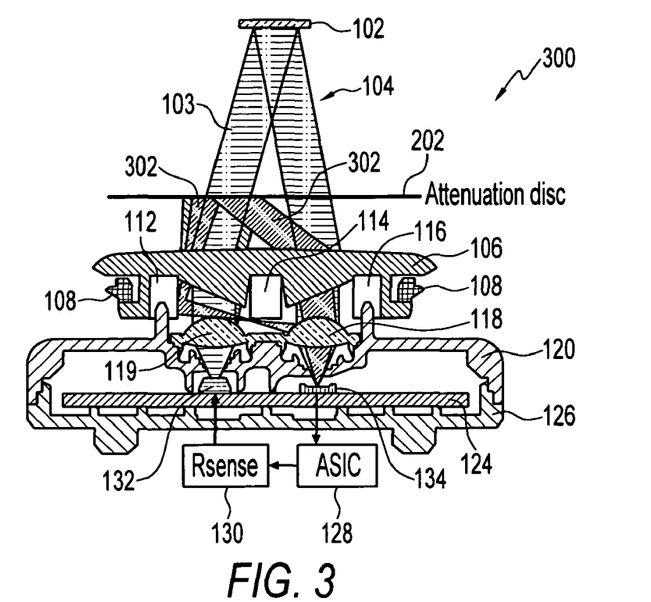
FIG. 3 illustrates a cross-sectional view of an optical keyless entry sensor system, which can be implemented in accordance with an preferred embodiment.

FIG. 3 illustrates a cross-sectional view of an optical keyless entry sensor system 300, which can be implemented in accordance with a preferred embodiment. Note that in FIGS. 1-3, identical or similar parts or elements are generally indicated by identical reference numerals. Thus, system 300 represents a modification to the sensor system 100 depicted in FIG. 3 and can be adapted for use in accordance with the system 300 in place of or as a modification to the sensor 100. System 300 thus represents a modification of sensor 100.

When the attenuation filter 202 covers both sides of the transmitter (i.e., IR LED 132) and the receiver (i.e., photodiode 134) of the keyless entry sensor 300 shown in FIG. 3, the measured dynamic range is much lower than the actual value due to cross-talk of lights between the transmitter (i.e., IR LED 132) and the receiver (i.e., photodiode 134). The reason this is so is because the light from the transmitter side will partly reflect back to the transmitter side. Because the light after passing through one of dual lenses 118, 119 are not perfectly collimated, part of the reflective lights back to the transmitter will hit other components of the sensor as shown by section 302 depicted in FIG. 3. Due to specular and scattering effects of the inner structure of the sensor 300, some of these lights could come into contact with the photodiode 134. On the other hand, the reflective filter 202 may function to reflect part of the light directly into the receiver as shown by section 302 in FIG. 3, which can also cause a reduction of the measured dynamic range.

Figure 4:
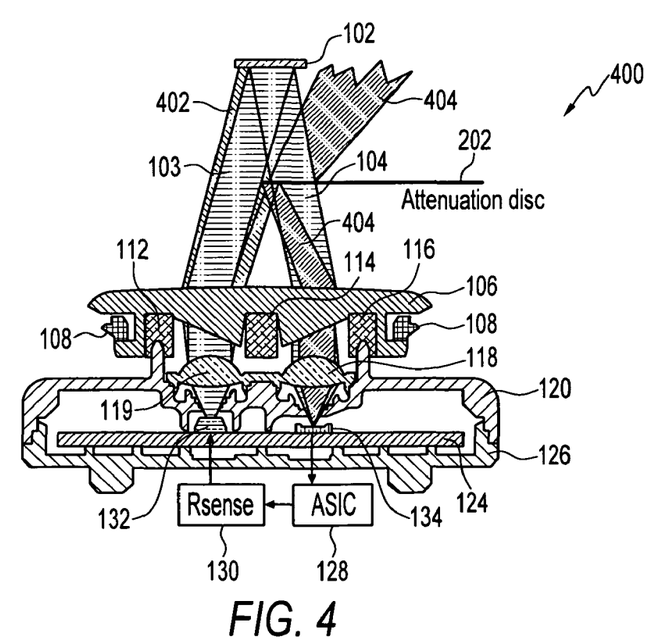
FIG. 4 illustrates a cross-sectional view of an optical keyless entry sensor system, which can be implemented in accordance with another embodiment.

FIG. 4 illustrates a cross-sectional view of an optical keyless entry sensor system, which can be implemented in accordance with another embodiment. Note that in FIGS. 1-4, identical or similar parts or elements are generally indicated by identical reference numerals. Thus, system 400 represents a modification to the sensor systems 100 and 300. Such systems 100, 300 can be adapted for use in accordance with the system 400. Note that system 400 thus represents a modification to systems 100 and/or 300, depending upon design considerations.

As indicated in FIG. 4, the attenuation filter 202 can be arranged in a manner that covers the receiver or photodiode 134 of system 400 in order to overcome the reflective lights from the attenuation filter 202 into the photodiode 134 during testing of the dynamic range system 400. As depicted in FIG. 4, when the light 104 from the mirror 102 hit the attenuation filter or disc 202, a part of the light reflected by the attenuation filter can be diverted away without any attribution to cross-talk as indicated by a light section 404, thereby avoiding some of the measurement error caused by the configuration depicted in FIG. 2. Because light, however, from the transmitter side of sensor 400 is may not be perfectly collimated, part of the diverged light from the transmitter (i.e., IR LED 132) of the sensor 400 may hit on the attenuation filter 202 and then reflect back to the photodiode 134, as shown by the light section 404 depicted in FIG. 4, which may result in a measurement error of the dynamic range value.

Figure 5:
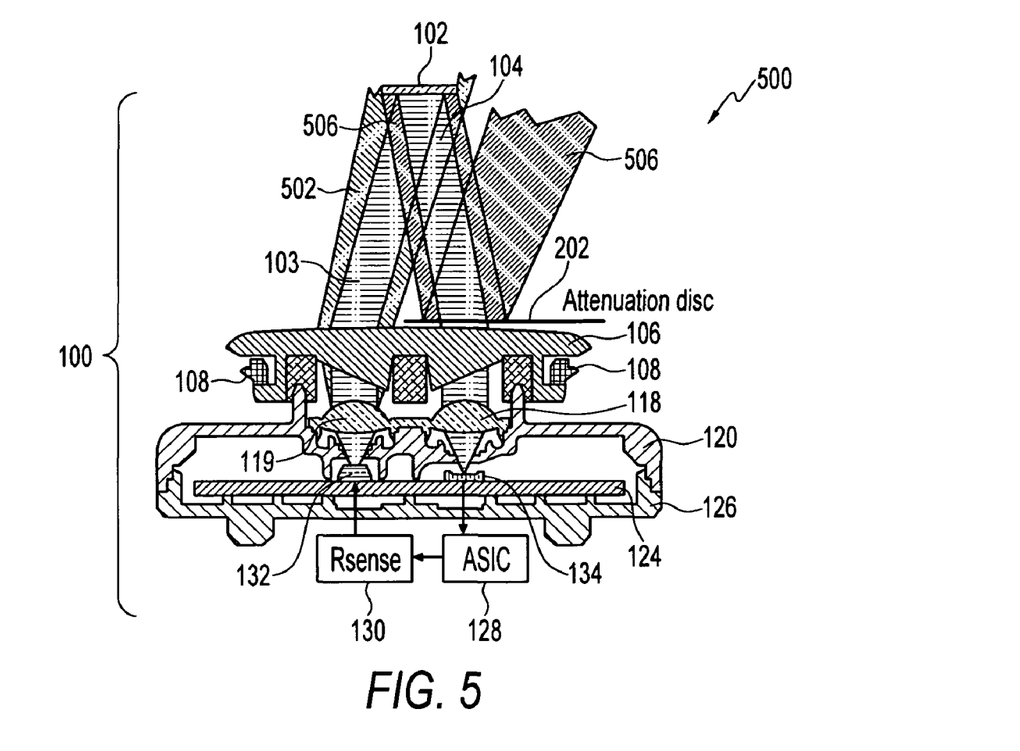
FIG. 5 illustrates a cross-sectional view of an optical keyless entry sensor system, which can be implemented in accordance with an additional embodiment.

FIG. 5 illustrates a cross-sectional view of an optical keyless entry sensor system 500, which can be implemented in accordance with an additional embodiment. Note that in FIGS. 1-5, identical or similar parts or elements are generally indicated by identical reference numerals. Thus, system 500 represents a modification to the sensor systems 100, 300, 400. Such systems 100, 300, 400 can be adapted for use in accordance with the system 500. Note that system 500 thus represents a modification to systems 100, 300 and/or 500, depending upon design considerations.

In order to avoid any the possibility of reflective lights from the reflective continuous attenuation neutral density filter 202 coming contact with the photodiode 134, the attenuation filter 202 should preferably be set as close as possible to the receiver or photodiode 134 as depicted in FIG. 5. Note that light section 502 represents variations from light 103. In practice, the air gap between the sensor and the filter can be approximately 0.5 mm depending upon design considerations. Such an arrangement can entirely avoid any sort of reflective lights (i.e., depicted by light sections 506) from the reflective continuous attenuation neutral density filter 202 into the photodiode 134, while fulfilling the accurate dynamic range measurement of the sensor 500.

Figure 6:
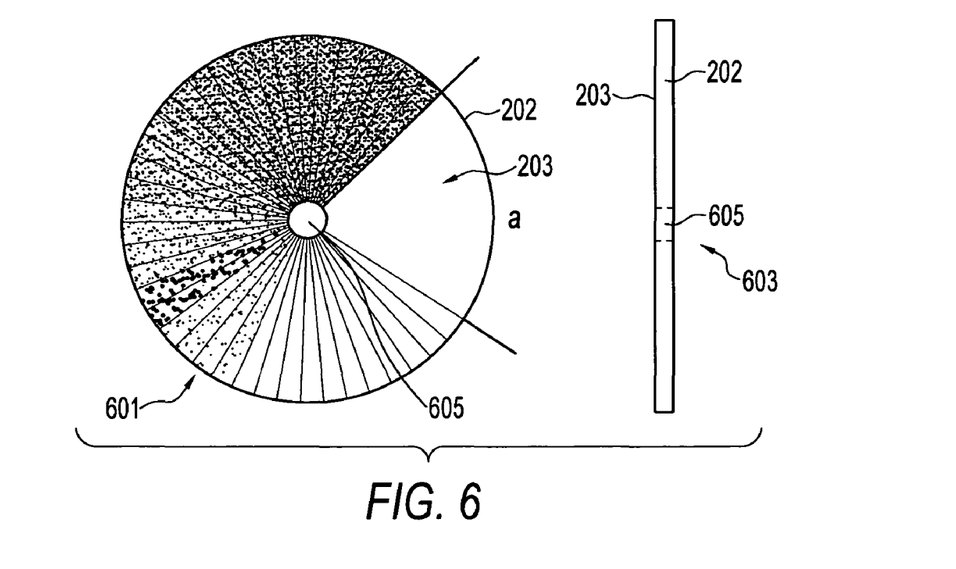
FIG. 6 illustrates top and side views of a reflective continuous attenuation neutral density filter, which can be implemented in accordance with a preferred or alternative embodiment.

FIG. 6 illustrates top 601 and side 603 views of the reflective continuous attenuation neutral density filter or disc 202, which can be implemented in accordance with the preferred or alternative embodiments disclosed herein. In general, filter 202 includes a central gap 605 and a top portion 203. The structure of one possible shape of filter 202 is thus shown in FIG. 6. Although illustrated as circular in shape, it can be appreciated that filter 202 may be implemented in the context of other shapes—square, rectangular, irregular, and so forth, depending upon design considerations.

Figure 7:
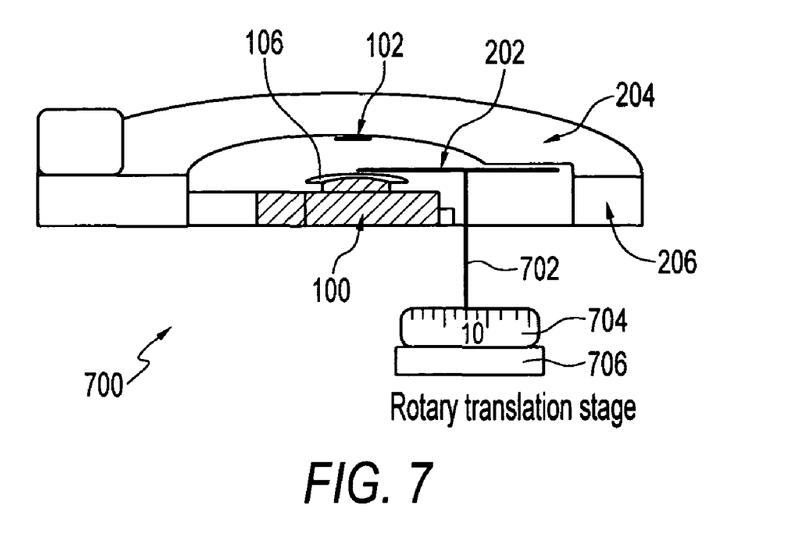
FIG. 7 illustrates a cross-sectional view of a system that can be implemented to measure the dynamic range of an optical keyless entry sensor device, in accordance with an embodiment.

FIG. 7 illustrates a cross-sectional view of a system 600 that can be implemented to measure the dynamic range of the optical keyless entry sensor devices or systems 100, 300, 400, and 500 discussed earlier, in accordance with an embodiment. Note that in FIGS. 1-7, identical or similar parts or elements are generally indicated by identical reference numerals. System 600 represents a modification to system 200 described and illustrated earlier herein. In system 600, the filter 202 is moved toward the right with respect to the mirror 102 and lens protector 106. A measurement device 704 is connected directly to the attenuation disk or filter 202 by an adapter shaft 702. A rotary transition stage is connected to the measurement device 704.

According to the rotational angle of the attenuation filter disc 202, the optical transmission value can be precisely calculated. For purposes of this example, the transmission rate without any attenuation can be assumed to be represented by the variable $T_{int}$. The tested transmission rate at the finished point in which the sensor just fails to function can be represented by the variable $T_{test}$. The dynamic range value d of the sensor can be calculated according to equation (1) below:

$$d = T_{int}/T_{test} \qquad (1)$$

This dynamic range represents the contamination-proof range of the sensor systems 100, 200, 300, 400, 500, and 700. Furthermore, linking the rotary angle with the real transmission rate can also be considered. Normally the suppliers of the continuous attenuation neutral density filters will specify optical density value rather than real transmission rate. Assume optical density at the starting point of the attenuation filter disc 202, in which the receiver aperture is located in an area, a, as shown FIG. 6, is $N_{int}$ and the reading angle of its start point from the rotary translation stage can be $\alpha_{int}$.

Figure 8:
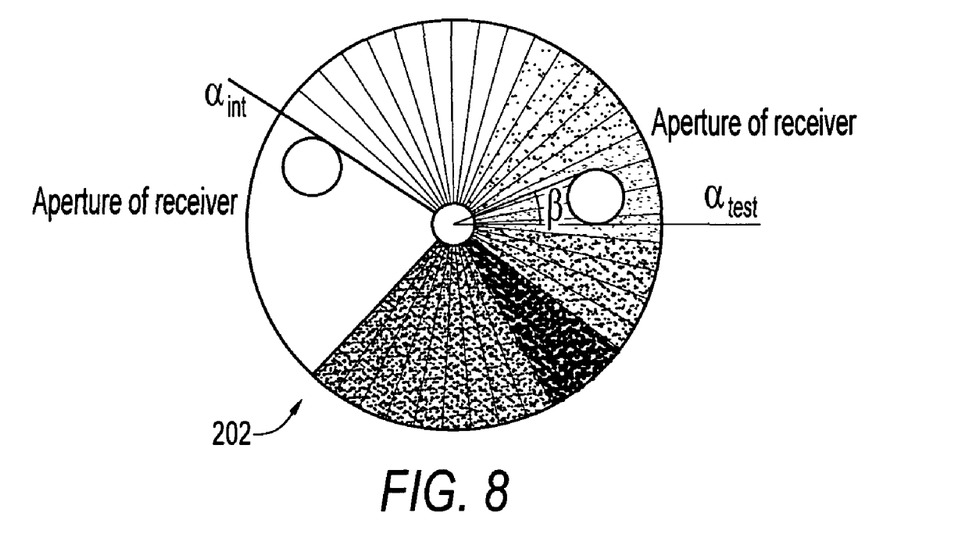
FIG. 8 illustrates a top view of the actual positions of starting and ending points associated with an attenuation filter that can be adapted for use in accordance with a preferred or alternative embodiment.

Also, the angle of a certain point referred to as the finished angle in the sensor, wherein the sensor just fails performance can be represented by the variable $\alpha_{test}$. The two angles are depicted in FIG. 8. In addition, assume the total attenuation area on this attenuation disc is R deg and its maximum optical density is N. Here R is less than 360 deg. The transmission rate of the filter 202 at the finished angle can then be calculated as follows:

$$T_{test} = 10^{-(N(\alpha_{test} - \alpha_{int})/R)} \quad (2)$$

FIG. 8 illustrates a top view of the actual positions of starting and ending points associated with the attenuation filter 202 that can be adapted for use in accordance with a preferred or alternative embodiment. As shown in FIG. 8, however, the calculated transmission rate of the sensor 100, 300, 400, or 500 at the finished point of the sensor 100, 300, 400, or 500 does not represent exact transmission rate due to non-zero aperture size of the receiver of the sensor 100, 300, 400, or 500. Assume the subtended angle by the receiver aperture is β. In order to obtain average transmission rate of the aperture, formula (2) can be re-written as $$T_{test} = \frac{10^{-(N(\alpha_{test} - \alpha_{int})/R)} + 10^{-(N(\alpha_{test} + \beta - \alpha_{int})/R)}}{2} \quad (3)$$

According to formula (1) and formula (3), the real dynamic range value d of the sensor 300, 400, or 500 should be as follows:

$$d = 2T_{int} / (10^{-(N(\alpha_{test} - \alpha_{int})/R)} + 10^{-(N(\alpha_{test} + \beta - \alpha_{int})/R)}) \quad (4)$$

As an example, consider an Edmund Optics K540-082 part selected as the reflective continuous attenuation neutral density filter in the test configuration of FIG. 7. In addition, an Edmund Optics K38-193 part can be chosen to be the rotary translation stage 706 to drive the filter 202 here β is 10 deg. R is 300 deg, $N_{int}$ is 0.04, N is 4.0.

Two generations of sensors, namely V1 for generation 1 and V2 for generation 2 have been developed. Two types of sensors are both aligned on the test jig for measurement of dynamic range values as indicated in Table 1 below. Table 1 thus demonstrates that the dynamic range values of V2 are better than those of V1.

TABLE 1

| Unit | Type of sensor | Starting angle | Finished angle | Transmission rate | Dynamic rate |
|---|---|---|---|---|---|
| RR1 | V1 | 25 | 148.6197 | 0.019696 | 46.30382 |
| RR2 | V1 | 25 | 144.6193 | 0.022263 | 40.96483 |
| 3 | V2 | 25 | 160.7898 | 0.013568 | 67.21698 |
| 4 | V2 | 25 | 161.8016 | 0.013154 | 69.33252 |
| 8 | V2 | 25 | 161.2869 | 0.013363 | 68.24815 |
| 11 | V2 | 25 | 162.8869 | 0.012724 | 71.67557 |
| 12 | V2 | 25 | 163.4617 | 0.012502 | 72.94833 |
| 16 | V2 | 25 | 162.7742 | 0.012768 | 71.42857 |
| 19 | V2 | 25 | 155.071 | 0.016165 | 56.41819 |
| 20 | V2 | 25 | 154.5738 | 0.016413 | 55.56571 |
| 24 | V2 | 25 | 154.5738 | 0.016413 | 55.56571 |
| 28 | V2 | 25 | 157.5526 | 0.014982 | 60.87305 |
| 31 | V2 | 25 | 157.5526 | 0.014982 | 60.87305 |
| 32 | V2 | 25 | 159.386 | 0.014164 | 64.38859 |

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. An optical entry sensor system, comprising:
   an optical transmitter for transmitting a source beam of light along a source beam of light path;
   a mirror, which reflects the source beam of light transmitted from said optical transmitter, resulting in a reflected beam of light that travels along a reflected beam of light path;
   an optical receiver situated adjacent to the optical transmitter, the optical receiver for receiving the reflected beam of light from the mirror;
   a movable attenuation filter that is positioned in the path of the reflected beam of light but not substantially in the path of the source beam of light, wherein said movable attenuation filter is rotatable to produce different amounts of attenuation to the reflected beam of light before the reflected beam of light reaches the optical receiver; and
   wherein said attenuation filter is rotated until the optical entry sensor system does not function properly, such that a measurement of a specific rotation angle of said attenuation filter, which is proportional to an attenuation value, represents a measure related to a dynamic range of said optical entry sensor system.

2. The system of claim 1 wherein said attenuation filter comprises a continuous attenuation neutral density filter.

3. The system of claim 1 further comprising a plurality of lenses which collimate light transmitted from said optical transmitter and reflected to said optical receiver from said mirror.

4. The system of claim 1 wherein said optical transmitter comprises an infrared light emitting diode.

5. The system of claim 1 wherein said optical receiver comprises a photodiode.

6. The system of claim 1 wherein said attenuation filter is located within about 0.5 mm from said optical receiver.

7. The system of claim 1 wherein said attenuation filter is an attenuation disk that has a total attenuation area that spans R degrees, where R is less than 360 degrees.

8. An optical entry sensor system, comprising:
   an optical receiver;
   an optical transmitter for transmitting a beam of light to the optical receiver;
   a rotatable attenuation filter, wherein said rotatable attenuation filter is rotatable to produce different amounts of attenuation to the beam of light before the beam of light reaches the optical receiver; and
   wherein said rotatable attenuation filter is rotated until the optical entry sensor system does not function properly, such that a measurement of a specific rotation angle of said rotatable attenuation filter, which is proportional to an attenuation value, represents a measure related to a dynamic range of said optical entry sensor system.

9. The system of claim 8 wherein said optical transmitter comprises an infrared light emitting diode.

10. The system of claim 8 wherein said optical receiver comprises a photodiode.

11. The system of claim 8 further comprising a mirror that is positioned to reflect a source beam of light transmitted by the optical transmitter, resulting in a reflected beam of light which is directed toward the optical receiver, wherein said rotatable attenuation filter is positioned in the reflected beam of light but not substantially in the source beam of light.

12. The system of claim 8 wherein said rotatable attenuation filter disk has a total attenuation area that spans R degrees, where R is less than 360 degrees.

13. An optical entry sensor method, comprising:
providing an optical transmitter for transmitting a source beam of light along a source beam of light path;
locating a mirror proximate to said optical transmitter, wherein said mirror reflects the source beam of light transmitted from said optical transmitter, resulting in a reflected beam of light that travels along a reflected beam of light path;
providing an optical receiver situated adjacent to the optical transmitter, the optical receiver receiving the reflected beam of light from the mirror;
locating an attenuation filter in the path of the reflected beam of light but not substantially in the path of the source beam of light, wherein said attenuation filter is movable to produce different amounts of attenuation to the reflected beam of light before the reflected beam of light reaches the optical receiver;
moving the attenuation filter to produce different amounts of attenuation to the reflected beam of light before the reflected beam of light reaches the optical receiver;
monitoring an output of the optical receiver in response to the movement of the attenuation filter; and
determining a dynamic range of the optical entry sensor based, at least in part, on the movement of the attenuation filter and the output of the optical receiver.

14. The method of claim 13 wherein said attenuation filter includes a continuous attenuation neutral density filter.

15. The method of claim 13 wherein said attenuation filter is a rotatable attenuation filter disk that has a total attenuation area that spans R degrees, where R is less than 360 degrees.

16. The method of claim 13 further comprising providing a plurality of lenses which collimate light transmitted from said optical transmitter along the source beam of light path, and reflected light from said mirror along the reflected beam of light path to said optical receiver.

17. The method of claim 13 wherein the moving step includes rotating said attenuation filter until said optical entry sensor does not function properly, such that a measurement of a specific rotation angle of said attenuation filter, which is proportional to an attenuation value, represents a measure related to a dynamic range of said optical entry sensor.

18. The method of claim 15 further comprising:
locating said attenuation filter within about 0.5 mm of said optical receiver.

19. An optical entry sensor method, comprising:
providing an optical transmitter for transmitting a beam of light;
providing an optical receiver, the optical receiver receiving the beam of light;
locating an attenuation filter in the beam of light, wherein said attenuation filter is movable to produce different amounts of attenuation to the beam of light before the beam of light reaches the optical receiver;
moving the attenuation filter to produce different amounts of attenuation to the beam of light before the beam of light reaches the optical receiver;
monitoring an output of the optical receiver in response to the movement of the attenuation filter; and
determining a dynamic range of the optical entry sensor based, at least in part, on the movement of the attenuation filter and the output of the optical receiver.

* * * * *